& Kramer

United States Patent [19]
Bernhardt et al.

[11] 4,239,703
[45] Dec. 16, 1980

[54] PROCESS FOR THE PREPARATION OF TEREPHTHALIC, ISOPHTHALIC AND PHTHALIC DIALDEHYDES

[75] Inventors: Günther Bernhardt, St. Augustin; Gerhard Daum, Cologne, both of Fed. Rep. of Germany

[73] Assignee: Dynamit Nobel Aktiengesellschaft, Troisdorf, Fed. Rep. of Germany

[21] Appl. No.: 62,826

[22] Filed: Aug. 1, 1979

[30] Foreign Application Priority Data

Aug. 3, 1978 [DE] Fed. Rep. of Germany ....... 2834051

[51] Int. Cl.³ .............................................. C07C 45/29
[52] U.S. Cl. .................................................... 568/431
[58] Field of Search ........................................ 260/599

[56] References Cited

U.S. PATENT DOCUMENTS

| | | |
|---|---|---|
| 2,806,883 | 9/1957 | Mikeska et al. ...................... 260/599 |
| 2,864,865 | 12/1958 | Errede et al. ......................... 260/599 |
| 3,692,840 | 9/1972 | Frangatos ........................ 260/599 X |
| 4,140,722 | 2/1979 | Williams et al. ..................... 260/599 |

*Primary Examiner*—Bernard Helfin
*Attorney, Agent, or Firm*—Sprung, Felfe, Horn, Lynch & Kramer

[57] ABSTRACT

A process for the preparation of a terephthalic, isophthalic or phthalic dialdehyde is described by dehydrogenation of the corresponding xylylene glycol in the vapor phase at 250° to 500° C. The process is carried out in the presence of oxygen, water vapor and a dehydrogenation catalyst, suitably a silver dehydrogenation catalyst.

15 Claims, No Drawings

PROCESS FOR THE PREPARATION OF TEREPHTHALIC, ISOPHTHALIC AND PHTHALIC DIALDEHYDES

BACKGROUND OF THE INVENTION

1. Field of the Invention

This invention relates to a process for the preparation of isomeric phthalic dialdehydes from the corresponding xylylene glycols.

2. Discussion of the Prior Art

It is known to prepare terephthalic and isophthalic dialdehydes by alkaline hydrolysis of xylylene tetrahalides in accordance with German (BRD) Offenlegungsschrift (DOS) No. 2,339,086. However, there are many by-products which are difficult to separate.

Terephthalic and isophthalic dialdehydes may be produced by oxidation of xylylene in the liquid or vapor phase with the aid of chromic acid, for example, according to J. Thiele and E. Winter, Ann. 311 (1900), 353, or U.S. Pat. No. 3,597,485. However, the aldehyde yield is very low, and large amounts of chromic oxide sludge are troublesome.

The preparation of terephthalic and isophthalic dialdehydes by reduction of terephthaloyl and isophthaloyl chlorides with hydrogen in the presence of a palladium catalyst (K. W. Rosenmund, Ber. 54 (1921), 2888) is uneconomical because of the large amounts of catalyst required.

The oxidation of xylylene glycols with selenium dioxide according to Ber. 64 (1930), 261, is limited to the laboratory because of the high cost of the oxidizing agent.

Oxidation with nitric acid according to Journ. für prakt. Chem. 151 (1938), 254, requires large excesses of nitric acid and because of its strongly exothermic nature is difficult to control.

Many aldehydes can be produced on an industrial scale by gas phase dehydrogenation of alcohols with catalysts of copper, silver or zinc compounds. However, the process is essentially limited to low-boiling alcohols such as methanol or butanol, since good aldehyde yields are obtainable only with these. (See Houben-Weyl, Methoden der organischen Chemie [Methods of Organic Chemistry], 4th ed., vol. 7/1, p. 160).

High-boiling alcohols, and particularly benzyl alcohols, cannot be converted economically by that process. The benzaldehyde yield is low because benzyl alcohols form ethers at the requisite high dehydrogenation temperatures and the aldehydes produced split off carbon monoxide. Moreover, the catalyst is subject to tarring and soon loses its activity.

It has been proposed to carry out the dehydrogenation under vacuum and at temperatures of less than 300° C. in the presence of oxygen. The amount of oxygen must be less than 50 percent of the amount necessary for absorption of the hydrogen susceptible of evolving in the dehydrogenation. (R. R. Davies and H. H. Hodgson, Soc. 1943, 282–284; C. Mouren and G. Mignonac, Compt. rend. 170 (1920), 258–261, Compt. rend. 171 (1920), 652). However, while these measures do increase the yields, because of the low dehydrogenation temperature and the applied vacuum they also result in pronounced dilution of the reaction mixture as well as low space-time yields and therefore make for an uneconomical process.

It is not known whether the last-mentioned process lends itself to the production of dialdehydes from glycols. The dehydrogenation of the two hydroxyl groups of the molecule to aldehyde groups which here is required makes it appear likely that the yields will be poor and that the number of by-products will be substantially increased. The preparation of dialdehydes other than those of simple structure may be expected to pose considerable difficulties.

It is an object of the present invention, therefore, to provide an economical process which can be readily practiced also on the industrial scale and which permits the preparation of phthalic dialdehydes in high space-time yields.

SUMMARY OF THE INVENTION

In accordance with the invention, this object is accomplished by a process which comprises contacting a xylylene glycol in the gaseous phase in the presence of a dehydrogenation catalyst at normal pressure and at temperatures ranging from 250° to 500° C., with water vapor and oxygen. The phthalic dialdehydes so prepared can be separated from the so formed aqueous condensates and recovered pure by distillation or recrystallization.

Thus, phthalic dialdehydes can unexpectedly be prepared in the presence of water vapor. By this process, p- and m-xylylene glycols in particular may be reacted.

The process is performed by heating the xylylene glycols to temperatures preferably ranging from 300° to 450° C.

It is preferred that the amount of the oxygen be at least 50 percent, but not more than 150 percent, and most preferably between 100 and 130 percent, of the amount required to absorb the hydrogen susceptible of evolving in the dehydrogenation.

It was not predictable that a substantial increase in xylylene glycol conversion and in phthalic aldehyde yields could be obtained also when amounts of oxygen greater than 50 percent of that required for absorption of the hydrogen susceptible of evolving in the dehydrogenation are used, since according to Houben-Weyl, Methoden der organischen Chemie (1954), vol. VII/1, page 164, an amount of oxygen in excess of 50 percent results in the further oxidation to the acid at the expense of drastically reduced aldehyde yields.

Unless water vapor is used in addition, further oxidation of the phthalic aldehydes to dicarboxylic acids or phthalaldehydic acids, or even total oxidation to carbon monoxide or dioxide, occurs also in the present process with amounts of oxygen in excess of 50 percent of that required. Water vapor alone in the absence of oxygen essentially produces only a partial dehydrogenation of xylylene glycols to hydroxymethylbenzaldehydes. The simultaneous presence of oxygen and water vapor in the dehydrogenation of xylylene glycol thus is an important factor.

The oxygen used in the dehydrogenation may be in pure form or in mixture with inert gases but is advantageously in the form of air.

The water vapor used should be free of acidic or alkaline components. It can be advantageous for the dehydrogenation of xylylene glycols if a portion of the water vapor is produced in the course of the dehydrogenation in the reactor by the evaporation of water.

The molar ratio of water vapor to xylylene glycol should be comprised between 1:1 and 100:1, and preferably between 5:1 and 50:1.

Suited for use as dehydrogenation catalysts are particularly silver catalysts such as those described in Methoden der organischen Chemie, by Houben-Weyl, 4th ed., vol. 4/2, pp. 154 to 162, and vol. 7/1, p. 162 et seq, the disclosure of which is hereby incorporated specifically herein by reference.

The silver may be used in the form of chips, granules, wool, wire gauze or sponge silver. The catalyst is advantageously applied to a carrier such as pumice, inert beads, granulated silica or alumina. The silver may be applied to the carrier by impregnating it with appropriate silver salt solutions or by applying moist silver oxide hydrate to it, drying and reducing it in a hydrogen/nitrogen stream at between 200° and 250° C., or heating it in an oxygen stream above the decomposition points of the salts or of the oxide.

In the present process, silver catalysts may be readily regenerated in a short time and as often as desired by passing air or oxygen over them at temperatures between 300° and 500° C. The reactor may be provided with two catalyst beds which are alternately used in dehydrogenation and regenerated.

In place of silver, other metal catalysts, for example, copper catalysts, may be used. However, in the presence of oxygen, copper catalysts lose their activity after a short time due to oxidation. Besides, they must be regenerated with hydrogen. Thus the use of copper catalysts in the dehydrogenation of xylylene glycols is possible but is not preferred.

In the dehydrogenation of xylylene glycols, the procedure followed in practice is to pass the xylylene glycol vapor in mixture with water vapor and air over the preheated catalyst. The air and the water or the water vapor may also be introduced separately.

The catalyst is preferably arranged in a fixed bed; however, it may also be used in a fluidized bed.

The reactor is preferably a vertical or inclined tubular reactor whose mixing zone is externally heated. The reaction zone as such with the catalyst is advantageously constructed so that it may be heated externally and cooled by means of a cooling element. The xylylene glycols to be dehydrogenated may be charged to the reactor as melts or as solutions, in particular as aqueous solutions. Charging xylylene glycol and water together has the advantage that the evaporation of the relatively high-boiling glycols is easier and less rigorous than the evaporation of the xylylene glycols alone so that the formation of condensation products from the glycols and also from the reaction products is avoided.

The evaporation of the xylylene glycols can further be facilitated by introducing also superheated steam into the reactor along with the necessary oxygen or air.

The temperatures used to evaporate the xylylene glycol/water mixture are comprised between 250° and 500° C., and preferably between 300° and 450° C.

The reaction takes place at normal pressure or at slight sub-atmospheric pressure. Preferred are pressures ranging from 0.2 to 1.3 bars. The gaseous phthalic aldehydes diluted with water vapor which leave the reactor are preferably condensed simply by co-condensation of water vapor and product.

The phthalic aldehyde separated from the water may, after cooling, be separated by filtration and recovered pure, either by distillation, preferably under vacuum, or by recrystallization.

The aqueous filtrates contain a little unreacted xylylene glycol and possibly small amounts of hydroxymethylbenzaldehydes which when recycled also form dialdehydes. After reconcentration with fresh xylylene glycol, the filtrate can be fed back to dehydrogenation.

It is surprising that the methylol groups of xylylene glycol are dehydrogenated almost exclusively to aldehyde groups. It is also surprising that at the high temperatures of 250° to 500° C. there is no condensation of the aldehydes to polyesters and no polyether formation.

The yields of phthalic dialdehydes and the conversion of the xylylene glycols are excellent and, when the reaction is conducted properly, can be practically quantitative.

Special advantages of the process are: the high space-time yield, the fact that the process is ecologically harmless since there is virtually no exhaust air or waste water, and the process can be carried out continuously.

The xylylene glycol conversion is calculated by the formula $$\frac{\text{converted xylylene glycol}}{\text{xylylene glycol introduced}} \times 100,$$

and the yield by the formula $$\frac{\text{dehydrogenation product formed}}{\text{converted xylylene glycol}} \times 100.$$

Terephthalic and isophthalic dialdehyde are valuable intermediate products for organic syntheses. They are used in the manufacture of optical brighteners, light stabilizers and dyes.

In order to more fully illustrate the nature of the invention and the manner of practicing the same, the following examples are presented.

EXAMPLE 1

Set onto a vertically disposed steel pipe of a length of 110 cm and an inside diameter of 57 mm is a closure with two inlets, one for gas, the other for water vapor. The bottom of the pipe is closed by wire netting which in the center has a 2.5 cm wide cutout through which a 30 cm long cooling tube projects centrally so that an annular cylindrical reaction zone (zone I) is formed between the inner wall of the pipe and the cooling tube. The lower part of said zone is filled with coarse quartz pebbles in such a way that the bed placed thereon of 86 cc of catalyst of a particle diameter between 0.75 and 1.6 mm is flush with the upper end of the cooling tube. The catalyst consists of 50 wt. % silver on pumice, produced by rolling silver oxide onto the carrier, followed by reduction. The free volume of the catalyst layer is 52.4 cc.

The cylindrical space above said layer serves for the mixing and heating of the reactants and auxiliaries (zones II and III) and is filled with steel cylinders 1 cm long and 3 mm thick. Zones II and III, which in the present case are of equal length, are heated externally. Zone I is constructed so that it is adapted to be externally heated and cooled by the cooling tube. The temperature of all zones is measured by means of thermocouples.

Between zones II and III there is a lateral capillary-tube connection which extends as far as the pipe interior and serves for pumping in the xylylene glycol solution. Both the capillary and the pump head are heatable.

Through feed lines at the top of the pipe, nitrogen is introduced at the rate of 111.8 l/h, and water at the rate of 289.6 cc/h. Zones II and III are heated until temperatures between 350° and 355° C. prevail at the lower end of both zones.

After adjustment of the temperature, a 33.3 wt. % aqueous p-xylylene glycol solution heated to 70° C. is pumped in through the lateral capillary tube so that 132.5 g of xylylene glycol per hour is introduced into the reactor. The nitrogen now is replaced with an air stream of equal strength. Through adjustment of the heating of zone II, a temperature between 350° and 355° C. is maintained.

Through alternate heating and cooling, the dehydrogenation temperature in zone I is maintained at between 395° and 400° C.

After 22 hours' operation, the metering in of xylylene glycol solution is discontinued, the amount of water pumped in through the top is increased to 555 cc/h, and the air introduced is gradually replaced with nitrogen over a period of half an hour while the flow rate is maintained.

A total of 1.04 mols $O_2$ per mol of starting material is added.

The yellowish-brown terephthalic dialdehyde which has solidified in the receiver is separated from the aqueous mother liquor by filtration, washed with water, and dried. The melting point is 115.5° to 116° C. By reconcentrating filtrate and wash water to one-third of the volume, more dialdehyde is recovered. The total amount weighed out is 2.15 kg, the purity 98.1%. From this, a colorless product having a purity of better than 99.5% is obtained by vacuum distillation. (Boiling point, 128° to 129° C., 13 Torr.)

On the basis of gas-chromatographic analysis with the aid of a calibrating curve, the aqueous mother liquor contains 149 g p-xylylene glycol, 409 g p-hydroxymethylbenzaldehyde, and 61 g terephthalic dialdehyde.

The xylylene glycol conversion is 95.0%, the terephthalic aldehyde yield 80.0%.

In further batches carried out continuously in the same manner, the mother liquor of each preceding batch is used with its content of p-hydroxymethylbenzaldehyde in place of water. Based on the conversion of xylylene glycol, the dialdehyde yield then is 97 to 98%.

EXAMPLE 2

The dehydrogenation in accordance with Example 1 was repeated, except that only half the volume of the catalyst named in that example was used, the dehydrogenation temperature was raised to between 410° and 415° C., and the air feed rate was increased to 130 l/h.

The xylylene glycol conversion was 95.2%, and the terephthalic dialdehyde yield 82.1%.

The aqueous mother liquor from the above workup was then reused in a further batch, the amount converted being replaced by the addition of p-xylylene glycol. This solution was concentrated by evaporation to 8.75 l and pumped into the reactor over a period of 22 hours.

The total yield of terephthalic dialdehyde was 13.27 kg, or 96.5%, based on the overall p-xylylene glycol conversion of 99.0%. The purity was 97.1%.

After distillation at reduced pressure (boiling point, 131° to 132° C.) 15 Torr, a colorless product (purity, better than 99.5%; melting point, 116° to 116.5° C.) was obtained.

EXAMPLE 3

Through the dehydrogenation reactor described in Example 1, whose catalyst in this case consisted of 130 cc of a silver/pumice catalyst with 30 wt. % silver of a particle diameter between 1.2 and 1.8 mm, a 33.3 wt. % aqueous m-xylylene glycol solution was passed over a period of 22 hours at such a rate that the hourly throughput of m-xylylene glycol through the catalyst bed was 133 g. In addition, air was introduced into zone III at the rate of 115 l/h, and water at the rate of 290.5 cc/h.

The dehydrogenation temperature was between 375° and 380° C. The reaction mixture was worked up as in Example 1.

The conversion was 98%, and the isophthalic dialdehyde yield 2.26 kg, or 81.3%. The purity was 98.4%.

After vacuum distillation, the purity was better than 99.5%. The melting point was 89° to 90° C.

EXAMPLE 4

Through the dehydrogenation reactor described in Example 1, which had a catalyst bed of 61.8 cc (209.1 g) of silver crystals (manufactured by Doduco Chemie) (free volume of catalyst layer, 40 ml), a 20 wt. % p-xylylene glycol solution was passed over a period of 8 hours at such a rate that the hourly p-xylylene glycol throughput through the catalyst zone was 66.3 g. In addition, air was introduced into zone II at the rate of 115 l/h, and water at the rate of 290 cc/h.

The dehydrogenation temperature was between 390° and 395° C.

The p-xylylene glycol conversion was 99.4%, and the terephthalic aldehyde yield 420 g, or 82.1%.

After vacuum distillation, the melting point was 115.5° to 116° C. and the purity better than 99.5%.

EXAMPLE 5

Example 2 was repeated, equal volumes of catalyst being used which consisted (a) of 35 wt. % silver on asbestos and (b) of 25 wt. % silver on shaped ceramic bodies.

Comparative Example A

The dehydrogenation of p-xylylene glycol was carried out as in Example 1, except that the molar ratio of p-xylylene glycol to atmospheric oxygen was 1:0.2.

The xylylene glycol conversion was 80.5%, the terephthalic aldehyde yield 998 g, or 43.8%.

It is apparent that a reduced amount of oxygen results in a reduced yield.

Comparative Example B (without the addition of water)

Through the two feed lines at the top of the reactor described in Example 1, 671 l/h nitrogen and 120 l/h air were introduced. In catalyst zone I, 43 cc of silver/pumice catalyst (silver content, 50 wt. %) of a particle size between 0.75 and 1.6 mm was disposed. Through a double-walled dropper funnel set onto the lateral inlet and heated with oil to 130° C., p-xylylene glycol was added dropwise at the rate of 135 g/h.

Temperatures: Zone I: 400° to 410° C. Zone II: 360° to 370° C. Zone III: 355° to 360° C.

In the upper portion of the cooling tube, a black, tarlike product was formed, and in the lower portion, a whitish coating.

Dehydrogenation had to be discontinued after a short time because the catalyst zone had become plugged.

The yellowish-white coating was found to be formed of a mixture of terephthalic acid and terephthalic aldehyde acid.

What is claimed is:

1. A process for the preparation of a terephthalic, isophthalic or phthalic dialdehyde which comprises heating a xylylene glycol in the vapor phase at a temperature between 250° and 500° C. in the presence of an oxygen-containing gas, water vapor, and in the presence of a silver dehydrogenation catalyst.

2. A process according to claim 1 wherein the xylylene glycol is heated at a temperature between 300° and 450° C.

3. A process according to claim 1 wherein the molar ratio of xylylene glycol to oxygen in the oxygen-containing gas is 1:0.5–1.5.

4. A process according to claim 3 wherein the molar ratio of xylylene glycol to oxygen is in the range of 1:1–1.3.

5. A process according to claim 1 wherein the molar ratio of xylylene glycol to water is in the range of 1:1–100.

6. A process according to claim 5 wherein the molar ratio of xylylene glycol to water is in the range of 1:5–50.

7. A process according to claim 1 wherein the process is carried out in the presence of an oxygen-containing and the oxygen-containing gas comprises air.

8. A process according to claim 1 wherein the silver is disposed on a catalyst carrier.

9. A process according to claim 8 wherein the catalyst carrier consists of inert material.

10. A process according to claim 9 wherein the inert material is pumice.

11. A process according to claim 1 wherein the dehydrogenation is carried out at atmospheric pressure or under a slight vacuum.

12. A process according to claim 11 wherein the dehydrogenation is carried out at a pressure of 0.2 to 1.3 bars.

13. A process according to claim 1 wherein the xylylene glycol is o-xylylene glycol.

14. A process according to claim 1 wherein the xylylene glycol is m-xylylene glycol.

15. A process according to claim 1 wherein the xylylene glycol is p-xylylene glycol.

* * * * *